United States Patent [19]

Quarroz

[11] Patent Number: 4,556,716
[45] Date of Patent: Dec. 3, 1985

[54] PROCESS FOR THE PRODUCTION OF 2-HALOPYRIDINE DERIVATIVES

[75] Inventor: Daniel Quarroz, Visp, Switzerland

[73] Assignee: Lonza Ltd., Gampel/Valais, Switzerland

[21] Appl. No.: 457,268

[22] Filed: Jan. 11, 1983

[30] Foreign Application Priority Data

Jan. 14, 1982 [CH] Switzerland .................... 194/82

[51] Int. Cl.$^4$ .................. C07D 213/26; C07D 213/55
[52] U.S. Cl. .................................. 546/345; 546/298; 546/318; 546/321; 546/326
[58] Field of Search ............... 546/345, 318, 321, 180, 546/298, 326

[56] References Cited

U.S. PATENT DOCUMENTS

| | | | |
|---|---|---|---|
| 3,153,044 | 10/1964 | Zaslowsky | 260/290 |
| 3,862,159 | 1/1975 | Umezawa et al. | 546/326 |
| 3,920,657 | 11/1975 | Beschke et al. | 260/290 |

FOREIGN PATENT DOCUMENTS 48-05591  2/1973  Japan .................................. 546/326

OTHER PUBLICATIONS

Murakami et al., Bul. Chem. Soc. Jap., 42, No. 11, (1969), pp. 3350 to 3352.
Boekelheide et al., J. Org. Chem., vol. 26, (Feb. 1961), pp. 428 to 430.
Chem. Abstr., 90, 174689e.
Chem. Abstr., 88, 141704m.

*Primary Examiner*—Joseph Paul Brust
*Attorney, Agent, or Firm*—Fisher, Christen & Sabol

[57] ABSTRACT

Process for the production of 2-halopyridine derivatives having the formula:

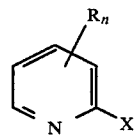

wherein X is halogen, R is —COOH or a lower alkyl radical and n is a number between 0 and 4. The corresponding 2-pyridine carboxylic acid-N-oxide derivatives having the formula:

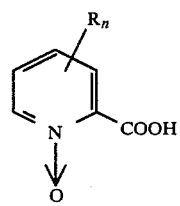

are reacted in the presence of an excess of organic anhydrides, tertiary alkylamines and a halogen-producing compound having the formula $CH_tX_m$, wherein t is 1 or 2, m is 2 or 3 and X is halogen, or having the formula $C_2H_pX_m$, wherein p is 3 or 4, m is 2 or 3 and X is halogen. The reaction mixture is adjusted to a pH value of 12 to 13 and the desired product is isolated from the mixture. Compound comprising (i) a 2-pyridine carboxylic acid-N-oxide derivative, (ii) an organic anhydride, (iii) a tertiary amine and (iv) a halogen-producing compound having the formula $CH_nX_m$. The composition can be used as the starting ingredients for the above process.

28 Claims, No Drawings

PROCESS FOR THE PRODUCTION OF 2-HALOPYRIDINE DERIVATIVES

BACKGROUND OF THIS INVENTION

1. Field of this Invention

This invention relates to a process for the production of 2-halopyridine derivatives having the formula:

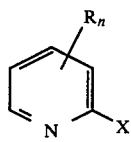

where X is halogen, R is —COOH or a lower alkyl radical and n is a number of 0 to 4.

2. Prior Art

2-Halopyridine compounds are accessible to numerous secondary reactions, since the halogen in the 2-position is relatively easily exchanged. For example, 2-chloro-5-pyridine carboxylic acid (6-chloronicotinic acid) serves as starting material for the production of 2-amino-5-pyridine carboxylic acid ester and amide (*Chem. Abst.*, 90, 174689 e; *Chem Abst.*, 88, 141704 m). A secondary product of 2-chloropyridine is pyridine-2-thiol-1-oxide (Omadine), an agent used against scales of the skin of the head. Furthermore, the 2-chloropyridine is an important intermediate product for numerous medicaments, for example, for antihistamines of the pheniramine-type. It is known to produce 2-chloropyridine derivatives, for example, 2-chloro-5-pyridine carboxylic acid (6-chloronicotinic acid), using PCl$_5$POCl$_3$, whereby hydroxynicotinic acid is produced, for example, from malic acid. The process is complicated and because of the use of phosphorus chloride compounds is accompanied by considerable effluent problems.

2-Chloropyridine is produced according to known processes by the gaseous phase chlorination of pyridine in the presence of water (U.S. Pat. No. 3,920,657) or carbon tetrachloride (U.S. Pat. No. 3,153,044) at temperatures around 350° C. The pyridine conversions are only around 34 to 50 percent. Unreacted pyridine is obtained as the hydrochloride and must be processed prior to reuse. Besides, other chlorination products also resulted which must be separated from the desired 2-chloropyridine.

BROAD DESCRIPTION OF THIS INVENTION

An object of this invention is to provide a process for the production of 2-halopyridine derivatives, especially 2-chloropyridine and 2-chloro-5-pyridine carboxylic acid, in a simple manner. Another object of this invention is to provide compositions from which such 2-halopyridine derivatives can be produced. Other objects and advantages of this invention are set out herein or are obvious herefrom to one ordinarily skilled in the art.

The objects and advantages of this invention are achieved by the processes and compositions of this invention.

This invention involves a process for the production of 2-halopyridine derivatives having the formula:

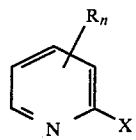

wherein X is halogen, R is —COOH or a lower alkyl radical and n a number between 0 and 4. The invention process includes reacting the corresponding 2-pyridine carboxylic acid-N-oxide-derivative having the formula:

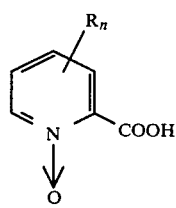

in the presence of an excess of an organic anhydride, a tertiary alkylamine and a halogen-producing compound having the formula CH$_t$X$_m$, wherein t is 1 or 2, m is 2 or 3 and X is halogen, or having the formula C$_2$H$_p$X$_m$, wherein p is 3 or 4, m is 2 or 3 and X is halogen. The reaction mixture is adjusted to a pH value of 12 to 13 and the resultant product is isolated from such mixture.

Acetic acid anhydride is the preferred organic anhydride; and triethylamine is the preferred tertiary amine. The halogen-supplying compound is preferably CH$_2$X$_2$, wherein X is chlorine, iodine or bromine. Preferably the halogen-supplying compound is used in an excess of 8 to 60 equivalents, in relation to 1 equivalent of the 2-pyridine carboxylic acid-N-oxide derivative. Preferably the anhydride is used at an excess of 1.2 to 3 equivalents, in relation to 1 equivalent of the 2-pyridine carboxylic acid-N-oxide derivative. Preferably the anhydride is put up with the tertiary amine and the halogen-supplying compound, and then the N-oxide derivative is added in doses. Another preferred way is to put up the N-oxide derivative with the teritary amine and the halogen-supplying compound with the anhydride then being added in doses. Preferably, when R is an alkyl radical, then 2-halopyridine is isolated from the reaction mixture by means of extraction. Also, preferably when R is —COOH, the 2-halopyridine carboxylic acid is precipitated by adjusting the reaction mixture to a pH-value of 1.5 to 2.

This invention also includes a composition for preparing 2-halopyridine derivatives. The invention composition includes (i) a 2-pyridine carboxylic acid-N-oxide derivative having the formula:

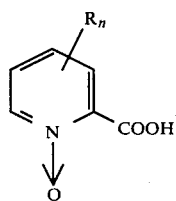

wherein R is —COOH or a lower alkyl radical and n is a number from 0 to 4, (ii) an organic anhydride, (iii) a tertiary amine and (iv) a halogen-producing compound having the formula $CH_nX_m$, wherein n is 1 or 2, m is 2 or 3 and X is halogen, or having the formula $C_2H_pX_m$, wherein p is 3 or 4, m is 2 or 3 and X is halogen. Components (ii), (iii) and (iv) each being present in an excess based upon component (i).

Preferably the organic anhydride is acetic acid anhydride, and preferably the tertiary amine is triethylamine. The halogen-producing compound preferably has the formula $CH_2X_2$, wherein X is chlorine, iodine or bromine. The halogen-producing compound preferably is present in an excess of 8 to 60 equivalents, based upon 1 equivalent of the 2-pyridine carboxylic acid-N-oxide derivative. The anhydride preferably is present in an excess of 1.2 to 3 equivalents, based upon 1 equivalent of the 2-pyridine carboxylic acid-N-oxide derivative.

DETAILED DESCRIPTION OF THIS INVENTION

The N-oxides of the 2-pyridine carboxylic acid themselves or the N-oxides of the derivatives therein are those which have additional substituents in the 3-, 4-, 5- and/or 6-position. Such N-oxides are, for example, those of isocinchomeronic acid, quinolinic acid, lutidinic acid, dipicolinic acid, α-carbocinchomeronic acid, α-carbodinicotinic acid, α'-carbisocinchomeronic acid, berberonic acid, 6-methylpicolinic acid, 6-ethylpicolinic acid, 4-methylpicolinic acid and others. Preferably the N-oxide of the isocinchomeronic acid is used for the production of the 6-chloro-nicotinic acid and the N-oxide of the picolinic acid for the production of 2-chloropyridine. Mixed anhydrides or pure anhydrides of low carboxylic acids having 1 to 4 carbon atoms can be used as the organic anhydrides. Examples of mixed anhydrides are formic acid-acetic acid anhydrides, acetic acid-propionic acid anhydride and acetic acid-butyric acid anhydride; and examples of pure anhydrides, are acetic acid anhydride, propionic acid anhydride and butyric acid anhydride. Acetic acid anhydride is preferred.

The anhydride is used in a large quantity such that there is a slight excess, advantageously 1.1 to 3 equivalents, per equivalent of the N-oxide in the reaction mixture.

As the tertiary amine, preferably a trialkylamine having 1 to 4 carbons is used. Examples of such are trimethylamine, triethylamine, tripropylamine and tributylamine. Triethylamine is preferably used and preferably in a quantity of 2 to 3 equivalents per equivalent of the N-oxide.

The halogen-supplying compounds are mostly the haloalkanes, where the H-atoms have not yet been completely replaced by halogen. $CHCl_3$, $CH_2Cl_2$, $CHCl_2CH_2Cl$, $CH_3CHCl_2$, $CH_2Br_2$, $CH_2I_2$, $CH_2Cl_2$, $CH_2Br_2$ and $CH_2I_2$ are preferred examples. It is important to use such halogen-supplying compounds in excess; effectively a quantity of 8 to 60 equivalents per equivalent of the N-oxide is used.

According to the process of this invention, a mixture of 2-halo and 2-hydroxy compounds is obtained. The greater the excess of halogen-forming compound which is used, the greater will be the formation of the desired 2-halo compound.

The reaction temperature has practically no influence on the yield. Effectively however the reaction is carried out at a temperature of 0° to 65° C. In the case of the use of higher temperatures (for example: 60° to 65° C., $CH_2Cl_2$), operation is advantageously conducted under pressure.

The process of this invention can be carried out without any foreign solvent or in the presence of a foreign (outside) solvent. Advantageously no foreign solvent is used, as the excesses of anhydride, amine and especially of a halogen-producing compound themselves act as the solvent.

Effectively the process of this invention is carried out such that either anhydride, amine and halogen-supplying compounds are put up and the N-oxide is added by doses, or the N-oxide, amine and halogen-supplying compound are put up and the anhydride is dosed in. The processing of this reaction mixture can be accomplished in two ways. According to one method, after the dosing in of the N-oxide or the anhydride, the halogen-supplying compound and the amine are distilled off and the pH of the solution is adjusted to a value of 12 to 13. Effectively, this is accomplished by the addition of an alkali hydroxide, perferably NaOH. The amine liberated thereby is distilled off and the aqueous solution is extracted in order to obtain the alkylated 2-halopyridine. For the isolation of the 2-halopyridine carboxylic acid, the aqueous solution is brought to the isoelectric point with hydrochloric acid. At the same time a mixture of 2-halo- and 2-hydroxypyridine carboxylic acid compound is precipitated, which subsequently can be separated by fractionated crystallization.

For the production of 2-halopyridine carboxylic acid with the other method, the reaction mixture, after the dosing in of the N-oxide or the anhydride, is brought to a pH of 12 to 13 without prior distillation, and the organic phase is drawn off and recirculated in a following batch. The aqueous solution is acidified and is processed further, as described above. The amine liberated thereby is distilled off and the aqueous solution is extracted for obtaining the alkylated 2-halopyridine. For the isolation of the 2-halopyridine carboxylic acid, the aqueous solution is brought to the isoelectric point with hydrochloric acid. At the same time a mixture of 2-halo- and 2-hydroxypyridine carboxylic acid compounds is precipitated, which subsequently can be separated by fractionated crystallization.

For the production of 2-halopyridine carboxylic acids according to another method, the reaction mixture, after dosing in the N-oxide or the anhydride, is brought without prior distillation to a pH of 12 to 13, and the organic phase is drawn off and recirculated in a next following batch. The aqueous solution is acidified and treated further as described above.

The starting compounds can be produced in any known manner. For example, for the production of N-oxide of the isocinchomeronic acid one starts out from 2-methyl-5ethylpyridine, which is transformed by oxidation into isocinchomeronic acid and finally is converted into the N-oxide by treatment with $H_2O_2$. The starting compounds are therefore easily accessible.

In the case where R is an alkyl radical, the isolation is accomplished effectively by extraction. In the case where R is a COOH radical, the isolation takes place effectively by adjusting the reaction mixture to a pH of 1.5 to 2, whereby the halopyridine carboxylic acid is precipitated.

By way of summary, 2-halopyridine derivatives are produced from the corresponding 2-pyridine carboxylic acid-N-oxides by the reaction of such N-oxides with haloalkanes in the presence of organic anhydrides and tertiary amines.

As used herein, all parts, ratios, percentages and proportions are on a weight basis unless otherwise stated herein or otherwise obvious herefrom to one ordinarily skilled in the art.

EXAMPLE 1

Production Of 6-Chloronicotinic Acid (6-ClNS) And 6-Hydroxynicotinic Acid (6-HNS) From Isocinchomeronic Acid-N-oxide 15.3 g of acetic acid anhydride (0.15 mole), 30 g of triethylamine (0.3 mole) and 200 g of $CH_2Cl_2$ (2.35 mole) were put into a flask. 18.3 of isocinchomeronic acid-N-oxide (0.1 mole) was added by doses at 40° C. in such a way that there was a lively development of $CO_2$. After the addition was completed, it was allowed to react again for about 1 hour at 40° C. until no more $CO_2$ escaped. The resultant light brown solution was concentrated on a rotavaporizer, and the viscous residue was treated by the addition of 10 percent NaOH (final pH was approximately 13) at about 80° C. for 1 hour. In order to remove the triethylamine, the liquid reaction mixture was distilled off and was subsequently acidified with concentrated HCl (pH of 1.5). The deposit obtained thereby was sucked off, was washed with $H_2O$ and was dried at 45° C. and 20 torr. The yield 13.1 g of product mixture (content of nicotinic derivatives was 97.2 percent; mole ratio of ClNS/HNS was 55/45) corresponded to a yield of 47 percent of 2-chloro-5-pyridine carboxylic acid (6-chloronicotinic acid) and 38.4 percent of 2-hydroxy-5-pyridine carboxylic acid (6-hydroxynicotinic acid), related to the amount of isocinchomeronic acid-N-oxide used.

EXAMPLE 2

This example proceeded as in Example 1, but with use of 500 g of $CH_2Cl_2$ and 0.3 mole of triethylamine. The yield of 13.9 g of product mixture (content of nicotinic derivatives was 98.5 percent; the ratio of ClNS/HNS was 64/36) corresponded to a yield of 58.1 percent of 6-chloronicotinic acid and 32.7 percent of 6-hydroxynicotinic acid, related to the amount of isocinchomeronic acid-N-oxide used.

EXAMPLE 3

This example proceeded as in Example 1, but the reaction was carried out at 0° to 5° C. the bath used had 25.5 g of $Ac_2O$, 20 g of $Et_3N$, 350 g of $CH_2Cl_2$ and 18.3 of isocinchomeronic acid-N-oxide. The yield was 53.8 percent of 6-chloronicotinic acid (2-chloro-5-pyridine carboxylic acid), and 39.0 percent of 6-hydroxynicotinic acid (2-hydroxy-5-pyridine-carboxylic acid).

EXAMPLE 4

A sludge of 50 g of $CH_2Cl_2$, 10 g of $Et_3N$ and 9.1 g of isocinchomeronic acid-N-oxide was placed in an autoclave. Under 4.5 atu. and at 65° C., a mixture of 10.2 g of $Ac_2O$, 5 g of $Et_3N$ and 50 g of $CH_2Cl_2$ was additionally pumped in. At the end of the addition, the reaction mixture was processed as in Example 1. The yield was 40.8 percent of 2-chloro-5-pyridine carboxylic acid (6-chloronicotinic acid) and 44.2 percent of 2-hydroxy-5-pyridine carboxylic acid (6-hydroxynicotinic acid).

EXAMPLE 5

36.6 g of $Ac_2O$, 60 g of $Et_3N$ and 600 g of $CH_2Cl_2$ were placed in a flask and heated at 40° C. 36.6 of isocinchomeronic acid-N-oxide was added in portions. After a further 1.5 hours, NaOH (10 percent) was added while strongly stirring until the final pH reached 13. The phases were separated. The $CH_2Cl_2$-solution was dried with solid NaOH and was kept for the next batch. The aqueous solution was acidified with concentrated HCl (final pH was about 2). The product obtained hereby was sucked off, washed and dried. The yield was 54.2 percent of 2-chlor-5-pyridine carboxylic acid (6-chloronicotinic acid) and 37.7 percent of 2-hydroxy-5-pyridine carboxylic acid (6-hydroxynicotinic acid).

To the dried $CH_2Cl_2$-phase (containing $Et_3N$), 30.6 g of $Ac_2O$ and 6 g of $Et_3N$ were added, which was supplemented with $CH_2Cl_2$ up to the volume of the first batch. Then 36.6 g of isocinchomeronic acid-N-oxide was added slowly at 40° C. As above, the nicotinic derivatives were isolated. The yield was the same as above, related to the newly used isocinchomeronic acid-N-oxide.

EXAMPLES 6 TO 12

| Ex. No. | Starting Material | Halogen Compound | Anhydride | Amine | Temperature | Yield |
|---|---|---|---|---|---|---|
| 6 | quinolinic acid-N—oxide 0.1 mole | $CHCl_3$ 500 g | acetic acid-butyric acid anhydride | triethyl amine | 40° C. | 47% 2-chloro nicotinic acid 7% 2-hydroxynicotinic acid |
| 7 | lutidinic acid-N—oxide 0.2 mole | $CH_2Cl_2$ 600 g | acetic acid anhydride | tributyl amine | 40° C. | 48% 2-chloro-isonicotinic acid 26% 2-hydroxy-isonicotinic acid |
| 8 | dipolinic acid-N—oxide 0.2 mole | $CH_2ClCHCl_2$ 600 g | acetic acid anhydride | triethyl amine | 40° C. | 13% 2-chloro-6-pyridine carboxylic acid 57% 2-hydroxy-6-pyridine carboxylic acid |
| 9 | 6-methylpicolinic acid-N—oxide 0.1 mole | $CH_2Cl_2$ 200 g | acetic acid anhydride | triethyl amine | 40° C. | 24% 2-chloro-6-picoline |
| 10 | picolinic acid-N—oxide 0.1 mole | $CH_2Cl_2$ 200 g | acetic acid anhydride | triethyl amine | 40° C. | 50% 2-chloropyridine |
| 11 | isocinchomeronic acid-N—oxide 0.1 mole | $CH_2Br_2$ 400 g | acetic acid anhydride | triethyl amine | 40° C. | 56% 2-bromo-5-pyridine carboxylic acid 26.6% 2-hydroxy- |

EXAMPLES 6 TO 12 -continued

| Ex. No. | Starting Material | Halogen Compound | Anhydride | Amine | Temperature | Yield |
|---|---|---|---|---|---|---|
| 12 | isocinchomeronic acid-N—oxide 0.1 mole | CH$_2$I$_2$ 500 g | acetic acid anhydride | triethyl amine | 40° C. | 5-pyridine carboxylic acid 35% 2-iodo-5-pyridine carboxylic acid 15% 2-hydroxy-5-pyridine carboxylic acid |

What is claimed is:

1. Process for the production of a 2-halopyridine derivative having the formula:

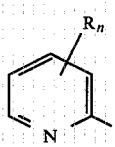

wherein X is halogen, R is —COOH or a lower alkyl radical, and n is 0 to 4, comprising (a) reacting (i) the corresponding 2-pyridine carboxylic acid-N-oxide derivative having the formula:

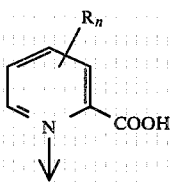

in the presence of (ii) an excess of at least one anhydride of a lower carboxylic acid having 1 to 4 carbon atoms, (iii) an excess of a trialkylamine each of said alkyl groups of said trialkylamine having 1 to 4 carbon atoms, and (iv) an excess of a halogen-producing compound having the formula CH$_t$X$_m$, wherein t is 1 or 2, m is 2 or 3 and X is a halogen selected from the group consisting of Cl, Br and I, or having the formula C$_2$H$_p$X$_m$, wherein p is 3 or 4, m is 2 or 3 and X is a halogen selected from the group consisting of Cl, Br and I, and in the liquid phase, (b) adjusting the reaction mixture in the liquid to a pH value of 12 to 13 and (c) isolating the resultant product from this mixture.

2. Process as claimed in claim 1 wherein said reaction is conducted at a temperature of 0° to 65° C.

3. Process as claimed in claim 1 wherein said at least one anhydride is selected from the group consisting of acetic acid anhydride, propionic acid anhydride, butyric acid anhydride, a mixture of formic acid-acetic acid anhydrides, a mixture of acetic acid-propionic acid anhydrides and a mixture of acetic acid-butyric acid anhydrides.

4. Process as claimed in claim 1 wherein said tertiary alkylamine is selected from the group consisting of trimethylamine, triethyalmine, tripropylamine and tributylamine.

5. Process as claimed in claim 1 wherein said halogen-supplying compound is selected from the group consisting of CHCl$_3$, CH$_2$Cl$_2$, CHCl$_2$CH$_2$Cl, CH$_3$CHCl$_2$, CH$_2$Br$_2$, CH$_2$I$_2$, CH$_2$Cl$_2$, CH$_2$Br$_2$ and CH$_2$I$_2$.

6. Process as claimed in claim 1 wherein acetic acid anhydride is used as said at least one anhydride.

7. Process as claimed in claim 1 wherein triethylamine is used as said trialkylamine.

8. Process as claimed in claim 1 wherein CH$_2$X$_2$, with X being chlorine, iodine or bromine, is used as said halogen-supplying compound.

9. Process as claimed in claim 1 wherein said halogen-supplying compound is used in an excess of 8 to 60 equivalents, in relation to 1 equivalent of said N-oxide.

10. Process as claimed in claim 1 wherein said at least one anhydride is used at an excess of 1.2 to 3 equivalents, in relation to 1 equivalent of said N-oxide.

11. Process as claimed in claim 1 wherein said at least one anhydride is mixed with said trialkylamine and said halogen-supplying compound, and then N-oxide is added in doses.

12. Process as claimed in claim 1 wherein said N-oxide is mixed with said trialkylamine and said halogen-supplying compound, and then said at least one anhydride is added in doses.

13. Process as claimed in claim 1 wherein, when R is a lower alkyl radical, then 2-halopyridines are isolated from the reaction mixture by extraction.

14. Process as claimed in claim 1 wherein, when R is —COOH, the 2-halopyridine carboxylic acid is precipitated by adjusting the reaction mixture to a pH value of 1.5 to 2.

15. Composition comprising: (i) a 2-pyridine carboxylic acid-N-oxide derivative having the formula:

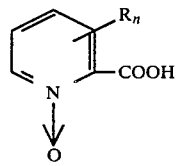

wherein R is —COOH or a lower alkyl radical and n is 0 to 4; (ii) at least one anhydride of a lower carboxylic acid having 1 to 4 carbon atoms, said at least one anhydride being present in an amount of 1.1 to 3 equivalents per equivalent of the 2-pyridine carboxylic acid-N-oxide derivative; (iii) a trialkylamine, each of said alkyl groups of said trialkylamine having 1 to 4 carbon atoms, said trialkylamine being present in an amount of 2 to 3 equivalents per 1 equivalent of the 2-pyridine carboxylic acid-N-oxide derivatives; and (iv) a halogen-producing compound having the formula CH$_n$X$_m$, wherein n is 1 or 2, m is 2 or 3 and X is a halogen selected from the group consisting of Cl, Br and I, or having the formula C$_2$H$_p$X$_m$, wherein p is 3 or 4, m is 2 or 3 and X is a halogen selected from the group consisting of Cl, Br and I, said halogen-producing compound being present in an amount of 8 to 60 equivalents per 1 equivalent of the 2-pyridine carboxylic acid-N-oxide derivative said components (i), (ii) and (iii) being in the liquid state.

16. Composition as claimed in claim 15 wherein said at least one anhydride is selected from the group consisting of acetic acid anhydride, propionic acid anhydride, butyric acid anhydride, a mixture of formic acid-acetic acid anhydrides, a mixture of acetic acid-propionic acid anhydrides and a mixture of acetic acid-butyric acid anhydrides.

17. Composition as claimed in claim 15 wherein said tertiary alkylamine is selected from the group consisting of trimethylamine, triethylamine, tripropylamine and tributylamine.

18. Composition as claimed in claim 15 wherein said halogen-supplying compound is selected from the group consisting of $CHCl_3$, $CH_2Cl_2$, $CHCl_2CH_2Cl$, $CH_3CHCl_2$, $CH_2Br_2$, $CH_2I_2$, $CH_2Cl_2$, $CH_2Br_2$ and $CH_2I_2$.

19. Composition as claimed in claim 15 wherein at least one anhydride is acetic acid anhydride.

20. Composition as claimed in claim 15 wherein said trialkyalmine is triethylamine.

21. Composition as claimed in claim 15 wherein said halogen-producing compound has the formula $CH_2X_2$, wherein X is chlorine, iodine or bromine.

22. Composition for the production of a 2-halopyridine derivative having the formula:

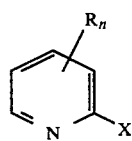

wherein X is halogen, R is —COOH or a lower alkyl radical, and n is 0 to 4, comprising: (i) a 2-pyridine carboxylic acid-N-oxide derivative having the formula:

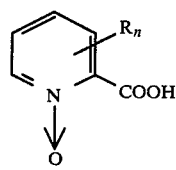

wherein R is —COOH or a lower alkyl radical and n is 0 to 4; (ii) at least one anhydride of a lower carboxylic acid having 1 to 4 carbon atoms, said at least one anhydride being present in an amount of 1.1 to 3 equivalents per equivalent of the 2-pyridine carboxylic acid-N-oxide derivative; (iii) a trialkylamine, each of said alkyl groups of said trialkylamine having 1 to 4 carbon atoms, said trialkylamine being present in an amount of 2 to 3 equivalents per 1 equivalent of the 2-pyridine carboxylic acid-N-oxide derivative; and (iv) a halogen-producing compound having the formula $CH_nX_m$, wherein n is 1 or 2, m is 2 or 3 and X is a halogen selected from the group consisting of Cl, Br and I, or having the formula $C_2H_pX_m$, wherein p is 3 or 4, m is 2 or 3 and X is a halogen selected from the group consisting of Cl, Br and I, said halogen-producing compound being present in an amount of 8 to 60 equivalents per 1 equivalent of the 2-pyridine carboxylic acid-N-oxide derivative, said 2-pyridine carboxylic acid-N-oxide, said at least one anhydride, said trialkylamine and said halogen-producing compound each being in a liquid state and each being present in an amount effective to collectively produce said 2-halopyridine derivative.

23. Compound as claimed in claim 22 wherein said at least one anhydride is selected from the group consisting of acetic acid anhydride, propionic acid anhydride, butyric acid anhydride, a mixture of formic acid-acetic acid anhydrides, a mixture of acetic acid-propionic acid anhydrides and a mixture of acetic acid-butyric acid anhydrides.

24. Compound as claimed in claim 22 wherein said tertiary alkylamine is selected from the group consisting of trimethylamine, triethylamine, tripropylamine and tributylamine.

25. Compound as claimed in claim 22 wherein said halogen-supplying compound is selected from the group consisting of $CHCl_3$, $CH_2Cl_2$, $CHCl_2CH_2Cl$, $CH_3CHCl_2$, $CH_2Br_2$, $CH_2I_2$, $CH_2Cl_2$, $CH_2Br_2$ and $CH_2I_2$.

26. Composition as claimed in claim 23 wherein said at least one anhydride is acetic acid anhydride.

27. Composition as claimed in claim 23 wherein said trialkylamine is triethylamine.

28. Composition as claimed in claim 23 wherein said halogen-producing compound has the formula $CH_2X_2$, wherein X is chlorine, iodine or bromine.

* * * * *